(12) United States Patent
Hardwick et al.

(10) Patent No.: US 6,471,247 B1
(45) Date of Patent: Oct. 29, 2002

(54) BANKNOTES INCORPORATING SECURITY DEVICES

(75) Inventors: Bruce Hardwick, Wandong (AU); Wayne Kevin Jackson, Reservoir (AU); Paul Zientek, North Carlton (AU); Cameron Rex Hibbert, Churchill (AU)

(73) Assignee: Securency Pty Ltd, Victoria (AU)

( * ) Notice: Subject to any disclaimer, the term of this patent is extended or adjusted under 35 U.S.C. 154(b) by 0 days.

(21) Appl. No.: 09/147,898

(22) PCT Filed: Sep. 24, 1997

(86) PCT No.: PCT/AU97/00632

§ 371 (c)(1),
(2), (4) Date: Aug. 19, 1999

(87) PCT Pub. No.: WO98/13211

PCT Pub. Date: Apr. 2, 1998

(30) Foreign Application Priority Data

Sep. 26, 1996  (AU) ............................................. PO2602

(51) Int. Cl.[7] ............................................. B42D 15/00
(52) U.S. Cl. ............................ 283/72; 283/82; 283/91; 283/111; 283/901
(58) Field of Search ........................... 283/72, 79, 81, 283/82, 91, 92, 94, 100, 101, 107, 110, 111, 68, 17, 73, 901; 428/611; 206/775, 776, 807

(56) References Cited

U.S. PATENT DOCUMENTS

| | | | | |
|---|---|---|---|---|
| 3,227,474 A | * | 1/1966 | Hoeflinger | |
| 4,296,326 A | * | 10/1981 | Haslop et al. | 250/372 |
| 4,536,016 A | * | 8/1985 | Solomon et al. | 283/111 |
| 5,093,184 A | | 3/1992 | Edwards | |
| 5,388,862 A | * | 2/1995 | Edwards | 283/82 |
| 5,393,099 A | | 2/1995 | D'Amato | |
| 5,492,370 A | * | 2/1996 | Chatwin et al. | 283/110 |
| 5,698,333 A | * | 12/1997 | Benoit et al. | 428/516 |
| 6,089,614 A | | 7/2000 | Howland et al. | |
| 6,210,777 B1 | * | 4/2001 | Vermeulen et al. | 283/72 |

FOREIGN PATENT DOCUMENTS

| | | |
|---|---|---|
| EP | 0 659 936 A2 | 12/1994 |
| GB | 2 250 473 A | 6/1992 |
| GB | 2 250 474 A | 6/1992 |
| WO | WO 83/00659 | 3/1983 |
| WO | WO 97/47478 | 12/1997 |

* cited by examiner

Primary Examiner—A. L. Wellington
Assistant Examiner—Monica Carter
(74) Attorney, Agent, or Firm—Christensen O'Connor Johnson Kindness PLLC

(57) ABSTRACT

A security document (1), such as a bank note, is formed from a sheet-like substrate (10) of clear plastic material with layers (13, 14, 15, 16) of opacifying ink applied to the surfaces (11, 12) of the substrate (10). The security document (1) includes a security device (20) which is at least partially obscured by the layers (13, 14) of opacifying ink on a flat surface (11) of the substrate (10). The layers (15, 16) on the second surface (12) of the substrate (10) are applied in such a manner so as to leave a "half-window" area uncovered by opacifying ink through which the security device (20) is visible for one side of the document (1). The security device (20) may extend transversely outside the half-window area and be visible in transmission, enabling a different contrasting effect to be observed from both sides of the document.

22 Claims, 2 Drawing Sheets

BANKNOTES INCORPORATING SECURITY DEVICES

TECHNICAL FIELD

This is a U.S. national stage application of International application No. PCT/AU97/00632, filed Sep. 24, 1997, the benefit of the filing date of which is hereby claimed under 35 U.S.C. §120, which in turn claims the benefit of Australian application No. PO 2602, filed Sep. 26, 1996, the benefit of the filing date of which is hereby claimed under 35 U.S.C. §119.

BACKGROUND OF THE INVENTION

This invention relates to security documents, such as banknotes or the like, and is particularly concerned with providing a security document formed from a plastic substrate with an enhanced security device.

In Australian Patent Specification No. AU-A-87665/82 there is disclosed a security document and a method of producing a security document, in which opacifying coatings of ink are applied to both sides of a sheet-like substrate formed from a clear plastics film. The security document may be produced with some areas to which no opacifying coating is applied on both sides of the clear plastics substrate. These clear, transparent areas are known as "windows" and are particularly suitable for incorporating security devices, for example diffraction gratings, optically variable devices and embossed images, which can be inspected in the transparent areas or windows from both sides of the security document. However, a security device, such as a diffraction grating, in a window generally has the same appearance when viewed from both sides of the security document.

It is therefore desirable to provide a security document which incorporates a security device that presents a different appearance from opposite sides of the document.

It is also desirable to provide a security document formed from a clear plastics substrate with an enhanced form of security device.

It is further desirable to provide a relatively simple method of providing a security document with an enhanced form of security device.

SUMMARY OF THE INVENTION

According to one aspect of the invention, there is provided a security document comprising:

a sheet-like substrate of clear plastics material having first and second surfaces on opposite sides of the substrate;

said substrate having a region including a security device;

at least one layer of opacifying ink applied on said first surface of the substrate and at least partially obscuring said security device from one side of the substrate; and at least one layer of opacifying ink applied on said second surface on the opposite side of the substrate in such a manner as to leave an area of the second surface which is not covered by the opacifying ink substantially in the region including the security device.

According to another aspect of the invention, there is provided a method of producing a security document comprising the steps of:

providing a sheet-like substrate of clear plastics material having first and second surfaces on opposite sides of the substrate;

said substrate being provided with a security device in at least one region of the substrate;

applying at least one opacifying layer of ink on said first surface of the substrate so as to obscure said security device from one side of the substrate; and applying at least one opacifying layer of ink to part of the second surface on the opposite side of the substrate in such a manner as to leave an area of the second surface of the substrate which is not covered by ink substantially in the region of the security device.

In the security document and method of the invention, the area of the second surface of the substrate which is not covered by the opacifying ink forms a "half-window" through which the security device may be inspected from one side of the substrate, the security device being at least partly obscured by the opacifying ink when viewed from the opposite side of the substrate. Thus the security device has a different appearance when viewed from opposite sides of the document.

For instance, the security device may be clearly visible in the half-window from the side of the second surface of the substrate, but not visible or only partially visible, e.g. only in transmission from the side of the first surface of the substrate. Preferably, the security device is more visible in transmitted light than in reflected light from the side of the first surface of the substrate.

The security device may be formed within the transparent plastics substrate. Alternatively, the security device may be applied to at least one of the first and second surfaces of the substrate.

In the method of the invention, the steps of applying the security device and of applying the layers of opacifying ink to the first and second surfaces of the substrate may be performed in different orders. For instance, the step of applying at least one layer of opacifying ink to part of the second surface of the substrate to form the half-window may be performed first before the steps of applying the security device to the substrate in the region of the half-window and of applying at least one opacifying layer to the first surface of the substrate to obscure the security device.

Preferably, however, the step of applying the security device to the substrate is performed prior to the steps of applying the layers of opacifying ink to the first and second surfaces of the substrate which may then be performed either simultaneously or one after another.

Preferably, part of the security device extends transversely outside the area of the "half-window" which is not covered by the opacifying ink on the second surface of the substrate. Preferably, the part of the security device which extends outside the area of the half-window is more visible in transmitted light than in reflected light. When a security device is provided in a banknote or security document in this manner, different parts of the security device may present different effects to a viewer from each side of the banknote or security document. For instance, if the layer or layers of opacifying ink only partially obscure the security device, the part of the security device outside the half-window area may be visible, at least in transmission, but not as apparent as the part of the security device within the area of the half-window. It is therefore possible for different contrasting effects to be observed between relative visibilities of the different parts of the substrate from both sides of the security document.

A wide variety of security devices may be employed in the present invention. Examples of the type of security devices which may be applied to the substrate in the present invention include: fine line or filigree patterns; micro-text; security stripes or threads; front and rear registration devices, including Moire patterns; embossings; diffracting gratings; optically variable devices; coloured, fluorescent, phosphorescent and pearlescent inks and optically variable inks; metameric inks, and coloured filters which may be used to view such inks.

When the security device comprises a front to back registration device, such as a Moire pattern, different parts of the device may be applied to the first and second surfaces on both sides of the clear plastics substrate before the opacifying layers of ink are applied.

Alternatively, the security device may comprise a taggant provided within the substrate. The taggant may be invisible to the naked eye, but readable by a reading device through the half-window from the side of the second surface of the substrate.

In one embodiment of the invention, the security document may have a plurality of half-windows which are not covered by opacifying ink. The plurality of half-windows may be provided on both sides of the substrate. For instance, both the first and second surfaces of the substrate may have half-window areas at different transverse locations that are not covered by opacifying ink, said half-window areas being arranged alternately on the first and second surfaces of the substrate. A continuous security device, such as at least one security stripe or thread may extend through the half-window areas to give the appearance of a stripe or thread weaving through the substrate.

BRIEF DESCRIPTION OF THE DRAWINGS

In order that the present invention may be more readily understood, various embodiments thereof will now be described, by way of example only, with reference to the accompanying drawings, in which.

DESCRIPTION OF THE PREFERRED EMBODIMENT

Figure 1:
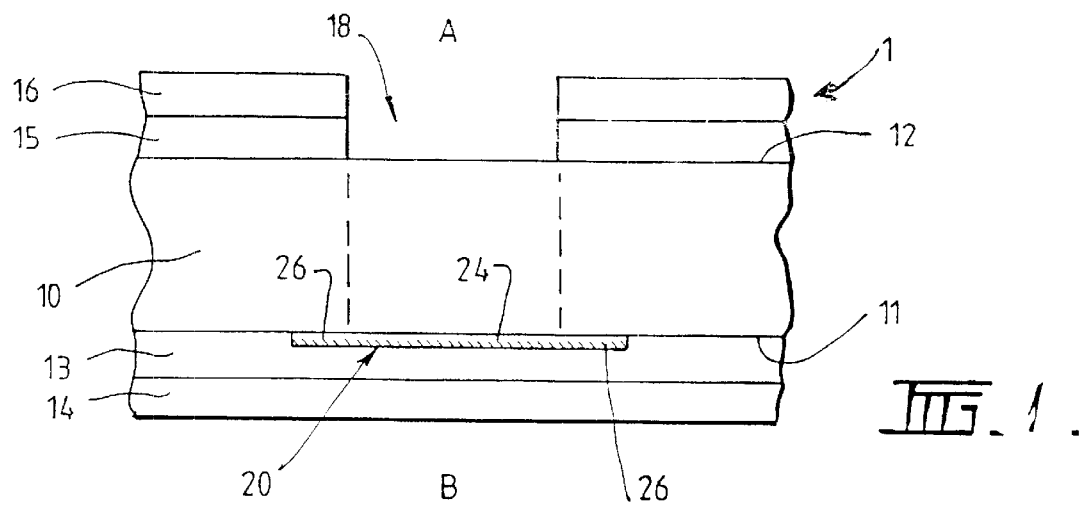
FIG. 1 is a sectional view through part of a security document in accordance with the invention.

In FIG. 1, there is shown a security document 1 comprising a sheet-like substrate 10 of clear plastics material having a first, lower surface 11 and a second, upper surface 12, layers 13 and 14 of opacifying ink applied on the first, lower surface 11 of the substrate 10, layers of opacifying ink 15 and 16 applied on the second, upper surface 12 of the substrate 10, and a security device 20 on the lower surface 11 of the substrate 10 between the substrate 10 and the layer of opacifying ink 13.

As shown in FIG. 1, the opacifying layers of ink 15 and 16 are not applied over the entire upper surface 12 of the substrate 10 and thus leave an area of the second, upper surface 12 which is not covered by opacifying ink to form a "half-window" 18 on one side of the substrate substantially in the region of the security device 20 which is applied to the first, lower surface 11 of the substrate 10.

The substrate 10 of clear plastics material preferably is formed from a transparent polymeric material which may be made up of at least one bi-axially-oriented polymeric film. The substrate may comprise a single layer film of polymeric material. Alternatively, the substrate may comprise a laminate of two or more layers of transparent bi-axially-oriented polymeric film of the type described in Australian Patent No. AU-A-87665/82, the contents of which are incorporated herein by reference.

The opacifying layers of ink 13, 14, 15 and 16 may comprise any one or more of a variety of opacifying inks which can be used in the printing of banknotes or other security documents. For example, the layers of opacifying ink may comprise pigmented coatings comprising a pigment, such as titanium dioxide, dispersed within a binder or carrier of heat-activated cross-linkable polymeric material as described in Patent Specification No. AU-A-87665/82.

Figure 2:
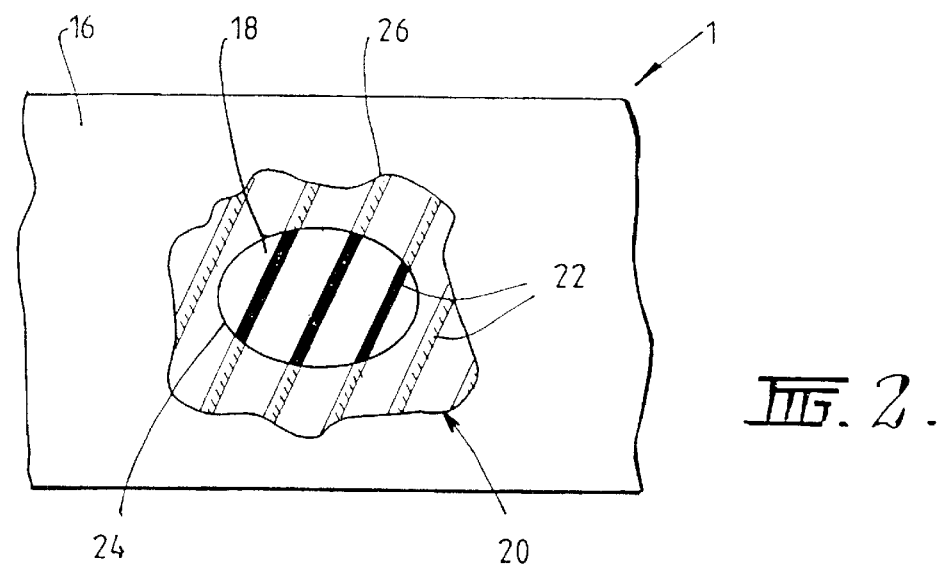
FIG. 2 is a view from one side of the security document of FIG. 1.
Figure 3:
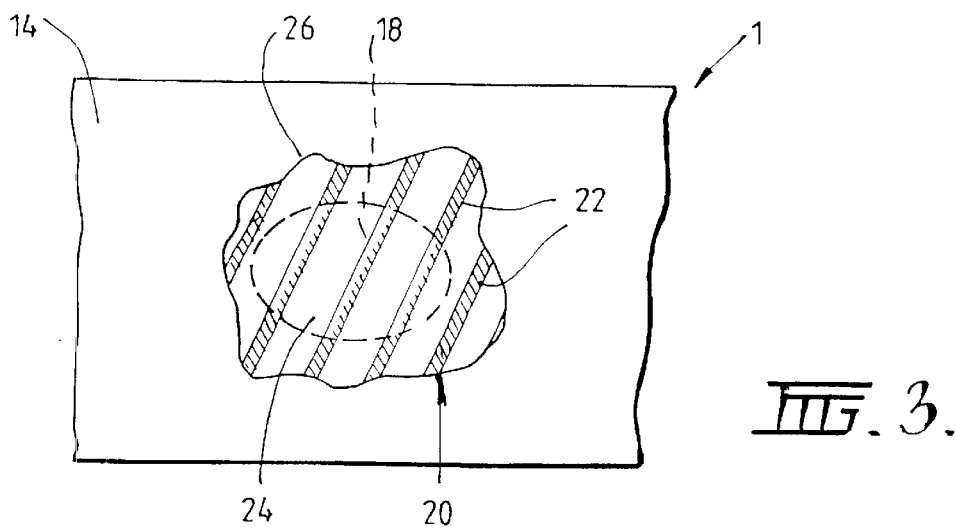
FIG. 3 is a view from the opposite side of the security document of FIG. 1.

The security device 20 may comprise one or more of a wide variety of security features. As shown in FIGS. 2 and 3, the security device 20 is a printed feature comprising a repeating pattern of lines 22 printed onto the first, lower surface 11 of the substrate 10. Other types of printed features which can be used as security devices in the present invention include varying patterns, such as filigree patterns of fine lines, micro-text, portraits or other images. The printed security feature may also be produced by including additives in the ink used to print the feature to create optical effects which can be used to enhance or add extra anti-counterfeiting security to the pattern or text. Thus, the inks used to print the security feature 20 could be coloured, fluorescent, phosphorescent, pearlescent or otherwise contain optically variable pigments or additives.

As shown in FIGS. 2 and 3, the printed security device 20 covers an area of the first, lower surface of the substrate 10 which extends transversely outside the area of the "half-window" 18 where there is no opacifying ink on the second surface 12 of the substrate 10. This can result in different optical effects as illustrated in FIGS. 2 and 3 when the security document is viewed from positions A and B respectively (see FIG. 1) on opposite sides of the document 1.

When the security device 20 is viewed from position A in reflected light, a central area 24 of the security device 20 is easily visible, but the outer area 26 of the security device 20 which extends beyond the area of the half-window 18 is either barely visible or not visible at all depending upon the opacity of the layers 15 and 16 of opacifying ink. When the security device is viewed from position B in reflected light, the whole of the security device 20 is barely visible or not visible at all depending upon the opacity of the layers 13 and 14 of opacifying ink.

FIG. 2 shows the security device when viewed in transmitted light from position A. In this case, the whole of the security device 20 is visible, but there is a contrast between the outer area 26 of the security device 20 because different amounts of light are transmitted through the document 1 inside and outside the half-window area 18.

FIG. 3 shows the security device 20 when viewed in transmitted light from position B. In this case, the whole of the security device 20 is also visible, but is not as readily visible as when viewed from position A because of the opacifying layers of ink 13 and 14 which cover the security device 20. However, because differing amounts of light are transmitted through the document inside and outside the half-window area 18, there is again a contrast between the relative visibilities of the central area 24 and the outer area 26 of the security device 20.

Figure 4:
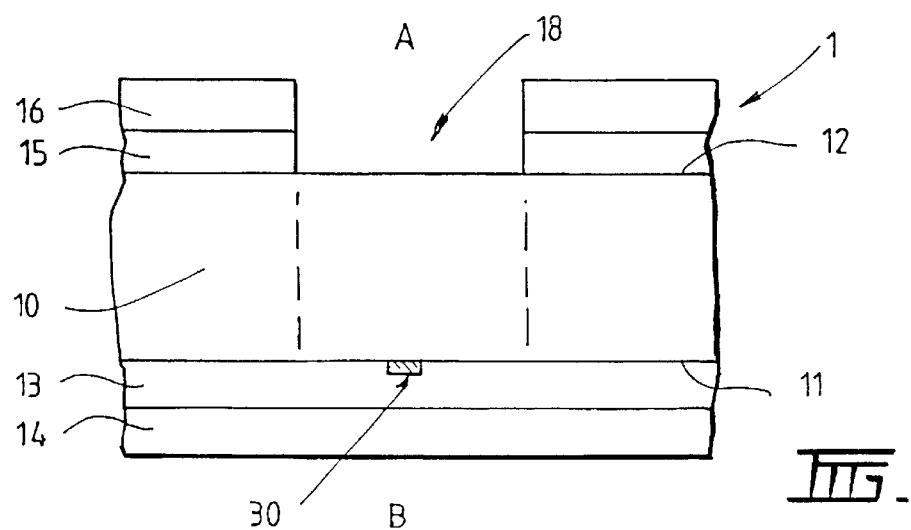
FIG. 4 is a sectional view through a security document in accordance with the invention incorporating a security thread.
Figure 5:
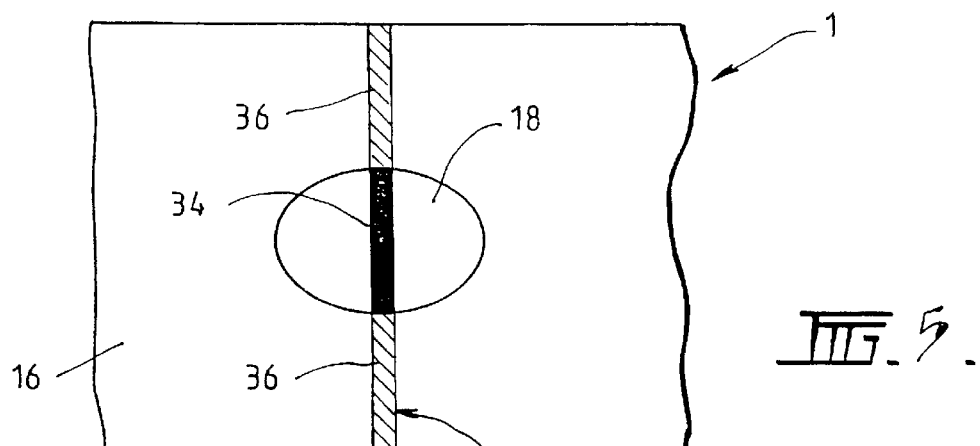
FIG. 5 is a view from one side of the security document of FIG. 4.

Referring to FIGS. 4 and 5, there is shown a security document 1 similar to the security document of FIG. 1, and corresponding reference numerals have been applied to corresponding parts. The security device 30 of FIGS. 4 and 5 differs from that of FIGS. 2 and 3 in that it comprises a security stripe or thread 30 applied to the first, lower surface 11 of the substrate 10 instead of the printed repeating pattern 20 of FIGS. 1 to 30. The security thread 30 may be formed from a metallic or plastics material which may be bonded to the first, lower surface 11 of the substrate 10. A metallic thread may be electrically conducting and/or magnetic. Alternatively, the security thread 30 may be printed onto the first, lower surface 11 of the substrate 10. It may be optically variable, fluorescent, phosphorescent or pearlescent and it may contain micro-text.

As shown in FIG. 5, the security thread 30 extends transversely outside the area of the half-window 18. Thus, when the security document 1 is viewed in transmitted light from position A, a central part 34 of the security thread 30 within the area of the half-window 18 is more readily visible than outer parts 36 of the security thread which extend outside the area of the half-window 18. A similar contrasting effect between the central part 34 and the outer parts 36 of the security thread 30 may be observed when the security document 1 is viewed in transmitted light from position B in FIG. 4, but the central part 34 of the thread will not be as readily visible when viewed from position B in transmitted light than when viewed from position A.

In a further embodiment of the present invention, the security device 20 applied to the first, lower surface of the substrate 10 may be an optically variable device (OVD) such as a hologram or diffraction grating. The OVD may be either fully or partially metallised.

It will be appreciated that a security document in accordance with the present invention with the security device 20 or 30 applied to the first, lower surface of the substrate and subsequently covered by one or more layers of opacifying ink 13 and 14, is difficult to counterfeit, whilst being readily inspectable in the half-window area. Another advantage of the invention is that the security device 20 or 30 is protected by being buried between the clear plastics substrate 10 and the opacifying ink layer or layers 13, 14. It should be understood that in transmitted light such security devices may be observed, and exhibit excellent fidelity, even when buried under opacifying layers of ink. This observation is a function of the non-fibrous nature of the opacifying ink coatings and is a distinct advantage over paper based fibrous layers.

A preferred method of producing a security document in accordance with the invention comprises the following steps:
(a) providing the sheet-like substrate 10 of clear plastics material;
(b) applying the security device to the first, lower surface 11 of the substrate;
(c) printing one or more opacifying layers of ink 13, 14 on the first, lower surface 11 of the substrate to cover the security device 20 or 30; and
(d) printing one or more opacifying layers 15, 16 of ink onto the upper surface 12 of the plastic substrate except in the half-window area 18 above the security device 20 or 30.

In the embodiment of FIGS. 2 and 3 where the security device 20 is a printed feature, the security device may be applied to the lower surface 11 of the clear plastics substrate 10 by using a gravure, offset or letter press printing process. Where the security device is either a fully or partially metallised feature such as a metallic thread 30 or an OVD, the metallic thread or OVD may be transferred onto the first, lower surface 11 of the plastics substrate 10 by using a hot-stamping process in which the security device bonds to the lower surface 11 of the substrate 10. If the security thread 30 of FIGS. 4 and 5 comprises a printed feature, it may be printed onto the first, lower surface 11 of the clear plastics substrate 10 using a gravure or offset process.

Figure 6:
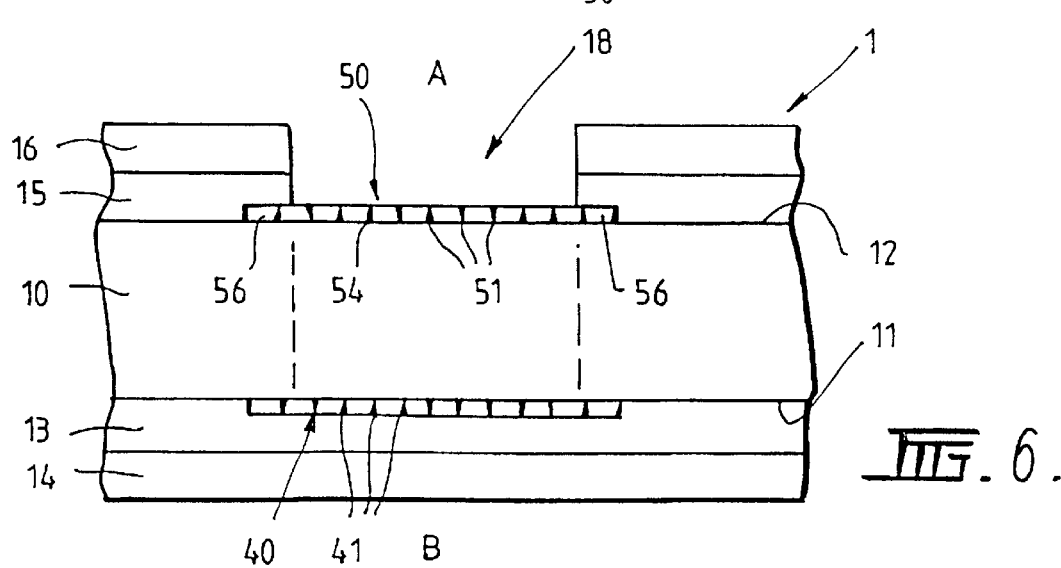
FIG. 6 is a sectional view through a security document in accordance with the invention incorporating a front-to-rear registration device.

Referring to FIG. 6, there is shown another embodiment of the present invention which is similar to the embodiments of FIGS. 1 and 4, and corresponding reference numerals have been applied to corresponding parts. The embodiment of FIG. 6 differs from FIGS. 1 and 4 in that it includes a front-to-back registration device comprising a first pattern 40 applied on the first, lower surface 11 of the clear plastics substrate 10 and a second pattern 50 applied on the second, upper surface 12 of the substrate 10.

The patterns 40 and 50 may comprise Moire patterns consisting of a series of lines 41, 51 having a predetermined spacing. When the security documents 1 is viewed in transmission from position A, and possibly also from position B, the combination of the two sets of lines 41 and 51 can product a Moire pattern due to interference effects. The security document of FIG. 6 is very difficult to counterfeit because the nature of the Moire pattern produced by the security device 40, 50 depends upon the predetermined spacing between the lines 41 and 51 of the patterns 40 and 50 and also upon the width of the clear polymer substrate 10 separating the patterns 40 and 50.

In a preferred method of producing the security document of FIG. 6, the series of lines 41 of pattern 40 may be printed onto the first, lower surface 11 of the clear plastics substrate 10 by using a gravure or offset process; the series of lines 51 of the pattern 50 are printed onto the second, upper surface 12 of the clear plastics substrate 10 in register with the lines 41 of pattern 40 preferably by using a gravure or offset printing process; and then one or more opacifying layers 13, 14; 15, 16 of ink can be printed onto the first and second surfaces 11 and 12 respectively of the clear plastics substrate 10 so that the layer or layers 13, 14 completely cover the pattern 40, with the layer or layers 15, 16 of ink being arranged to cover only a peripheral area 56 of the pattern 51 leaving a central area 54 of the pattern uncovered to form the half-window 18.

Another type of front-to-back registration device may include an area of metameric ink printed on the first lower surface of the substrate with a coloured layer applied to the second, upper surface of the substrate to form a coloured filter for viewing the area of metameric ink.

Further features of the half-window concept of the present invention which assist in preventing counterfeiting are that:
(i) the surface of the half-window is reflective in incident light, and is thus easily distinguishable from the printed area of the note; and
(ii) the tactility of the surface of the half-window is significantly different from the surrounding printed area.

It will be appreciated that various modifications may be made to the security documents and methods described above without departing from the scope and spirit of the present invention. For instance, the order in which the security devices 20; 30; 40, 50 and the opacifying layers of ink 13, 14, 15 and 16 are applied to the plastics substrate 10 may be varied, provided of course the security devices 20, 30 and 40 are applied to the first, lower surface of the substrate prior to application of the opacifying layers 13, 14 of ink.

What is claimed is:

1. A security document comprising:
   a sheet-like substrate of clear plastics material having first and second surfaces on opposite sides of the substrate;
   said substrate having a region including a security device;
   at least one layer of opacifying ink applied on a first side of the substrate; and
   at least one layer of opacifying ink applied on the opposite side of the substrate in such a manner as to leave an area on said opposite side which is not covered by the opacifying ink substantially in said region including the security device,
   wherein the at least one layer of opacifying ink applied on the first side of the substrate obscures the security device from the first side so that the security device is not visible in reflected light from said first side of the substrate.

2. A security document according to claim 1 wherein the appearance of the security device is different when viewed from opposite sides of the document.

3. A security document according to claim 1 wherein the security device is visible in transmitted light from the first side of the substrate.

4. A security document according to any one of claims 1 to 3 wherein part of the security device extends transversely outside said area of the second side which is not covered by the opacifying ink.

5. A security document according to claim 4 wherein said part of the security device extending transversely outside said area is more visible in transmitted light than in reflected light.

6. A security document according to any one of claims 1 to 3 wherein the security device comprises a security feature applied to at least one of the first and second surfaces of the substrate.

7. A security document according to claim 6 wherein the security device comprises a printed security feature.

8. A security document according to claim 6 wherein the security device comprises an embossing.

9. A security document according to claim 6 wherein the security device comprises a fully or partially metallised security feature.

10. A security document according to any one of claims 1 to 3 wherein the security device is provided within the substrate.

11. A security document according to claim 10 wherein the security device comprises a taggant within the substrate which is invisible to the naked eye, but readable by a reading device from the side of the second surface of the substrate.

12. A security document according to any one of claims 1 to 3 wherein the security device comprises an optically variable device.

13. A security document according to claim 6 wherein the security device comprises a front and rear registration device including a first device part applied to the first surface of the substrate and a second device part applied to the rear surface of the substrate.

14. A security document according to claim 13 wherein the first and second device parts of the front and rear registration device are Moire patterns.

15. A security document according to claim 7 wherein the security device includes an area of coloured, fluorescent, phosphorescent, pearlescent or optically variable ink applied to at least one surface of the substrate.

16. A security document according to claim 15 wherein the security device includes an area of metameric ink.

17. A security document according to claim 16 wherein the area of metameric ink is applied to the first surface of the substrate and a colored layer is applied to the second surface of the substrate to form a colored filter for viewing the area of metameric ink.

18. A security document according to claim 1 wherein the security device comprises at least one security stripe or thread.

19. A security document according to claim 18 wherein a plurality of areas of the second surface of the substrate are not covered by the opacifying ink and the security stripe or thread extends through said plurality of areas.

20. A security document according to claim 19 wherein both first and second surfaces of the substrates have areas which are not covered by opacifying ink, said areas being arranged alternately on the first and second surfaces and said security stripe or thread extending continuously or semi-continuously through said areas to give the appearance of a stripe or thread weaving through the substrate.

21. A security document according to claim 1 wherein the layers of opacifying ink are applied directly to said first and second surfaces of the substrate.

22. A security document according to claim 1 wherein the security device is visible in reflected light and in transmission when viewed from said opposite side of the substrate.

* * * * *